(12) United States Patent
Jamous et al.

(10) Patent No.: US 12,232,764 B2
(45) Date of Patent: Feb. 25, 2025

(54) TISSUE-REMOVING CATHETER WITH INNER LINER KEY

(71) Applicant: MEDTRONIC VASCULAR, INC., Santa Rosa, CA (US)

(72) Inventors: Aram Jamous, Athenry (IE); Tomas K. Kelly, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 381 days.

(21) Appl. No.: 17/671,409

(22) Filed: Feb. 14, 2022

(65) Prior Publication Data
US 2022/0287737 A1    Sep. 15, 2022

Related U.S. Application Data

(60) Provisional application No. 63/160,112, filed on Mar. 12, 2021.

(51) Int. Cl.
*A61B 17/00* (2006.01)
*A61B 17/32* (2006.01)
(Continued)

(52) U.S. Cl.
CPC ........ *A61B 17/320783* (2013.01); *A61B 17/320725* (2013.01); *A61B 17/320758* (2013.01);
(Continued)

(58) Field of Classification Search
CPC ........ A61B 17/3207; A61B 17/320758; A61B 17/320016; A61B 17/32002;
(Continued)

(56) References Cited

U.S. PATENT DOCUMENTS 5,134,407 A * 7/1992 Lorenz .................. G01S 19/24
342/352
6,010,407 A    1/2000 Ishikawa
(Continued)

FOREIGN PATENT DOCUMENTS

EP    3618734 A1    3/2020

OTHER PUBLICATIONS

"Telescopic Tubing, Apr. 8, 2019, Johnson Bros. Metal Forming Co., pp. 1-2" https://www.johnsonrollforming.com/display.php/display/c6/category/14 (Year: 2019).*
(Continued)

*Primary Examiner* — Kelly J Bekker
*Assistant Examiner* — Lindsey R. Rivers
(74) *Attorney, Agent, or Firm* — Stinson LLP

(57) ABSTRACT

A tissue-removing catheter for removing tissue in a body lumen includes an elongate body having an axis, and proximal and distal end portions spaced apart from one another along the axis. The elongate body is sized and shaped to be received in the body lumen. A handle is mounted to the proximal end portion of the elongate body. The handle includes a housing enclosing components operable to cause rotation of the elongate body. A tissue-removing element is mounted on the distal end portion of the elongate body. An inner liner is received within the elongate body and defines a guidewire lumen. An advancer is mounted on the handle and is movable relative to the housing. A guide tube is mounted in the handle and is coupled to the advancer such that movement of the advancer relative to the housing causes movement of the guide tube.

15 Claims, 13 Drawing Sheets

(51) Int. Cl.
*A61B 17/3207* (2006.01)
*A61B 17/22* (2006.01)

(52) U.S. Cl.
CPC ............... *A61B 2017/00318* (2013.01); *A61B 2017/00477* (2013.01); *A61B 2017/320052* (2013.01)

(58) Field of Classification Search
CPC .......... A61B 2017/00398; A61B 2017/00991; A61B 2017/320032
See application file for complete search history.

(56) References Cited

U.S. PATENT DOCUMENTS

| | | | |
|---|---|---|---|
| 6,464,632 | B1 | 10/2002 | Taylor |
| 11,819,236 | B2 * | 11/2023 | Kelly ............. A61B 17/320783 |
| 2018/0317954 | A1 * | 11/2018 | Jamous ............. A61M 25/0082 |
| 2020/0360047 | A1 | 11/2020 | Kelly et al. |

OTHER PUBLICATIONS

International Search Report and Written Opinion for PCT/US2022/019859, Aug. 9, 2022, 19 pages, Rijswijk, Netherlands.

* cited by examiner

TISSUE-REMOVING CATHETER WITH INNER LINER KEY

CROSS-REFERENCE TO RELATED APPLICATION

This application claims the benefit of U.S. Provisional Patent Application Ser. No. 63/160,112, filed on Mar. 12, 2021, the entire contents are hereby incorporated by reference.

FIELD

The present disclosure generally relates to a tissue-removing catheter, and more particular, to an inner liner assembly of a tissue-removing catheter.

BACKGROUND

Tissue-removing catheters are used to remove unwanted tissue in body lumens. As an example, atherectomy catheters are used to remove material from a blood vessel to open the blood vessel and improve blood flow through the vessel. This process can be used to prepare lesions within a patient's coronary artery to facilitate percutaneous coronary angioplasty (PTCA) or stent delivery in patients with severely calcified coronary artery lesions. Atherectomy catheters typically employ a rotating element which is used to abrade or otherwise break up the unwanted tissue.

SUMMARY

In one aspect, a tissue-removing catheter for removing tissue in a body lumen generally comprises an elongate body having an axis, and proximal and distal end portions spaced apart from one another along the axis. The elongate body is sized and shaped to be received in the body lumen. A handle is mounted to the proximal end portion of the elongate body. The handle includes a housing enclosing components operable to cause rotation of the elongate body. A tissue-removing element is mounted on the distal end portion of the elongate body. The tissue-removing element is configured to remove the tissue as the tissue-removing element is rotated by the elongate body within the body lumen. An inner liner is received within the elongate body and defines a guidewire lumen. An advancer is mounted on the handle and is movable relative to the housing. A guide tube is mounted in the handle and is coupled to the advancer such that movement of the advancer relative to the housing causes movement of the guide tube.

In another aspect, a tissue-removing catheter for removing tissue in a body lumen generally comprises an elongate body having an axis, and proximal and distal end portions spaced apart from one another along the axis. The elongate body is sized and shaped to be received in the body lumen. A handle is mounted to the proximal end portion of the elongate body. The handle comprises a housing enclosing components operable to cause rotation of the elongate body. A tissue-removing element is mounted on the distal end portion of the elongate body. The tissue-removing element is configured to remove the tissue as the tissue-removing element is rotated by the elongate body within the body lumen. A guide tube is mounted in the handle. An inner liner is received within the guide tube and is movable relative to the guide tube. The guide tube is configured to extend an effective length of the guide tube to accommodate movement of the inner liner in the guide tube.

In yet another aspect, a tissue-removing catheter for removing tissue in a body lumen generally comprises an elongate body having an axis, and proximal and distal end portions spaced apart from one another along the axis. The elongate body is sized and shaped to be received in the body lumen. A handle is mounted to the proximal end portion of the elongate body. The handle comprises a housing enclosing components operable to cause rotation of the elongate body. A tissue-removing element is mounted on the distal end portion of the elongate body. The tissue-removing element is configured to remove the tissue as the tissue-removing element is rotated by the elongate body within the body lumen. A guide tube is mounted in the handle. A liner assembly is coupled to the guide tube and is movable relative to the guide tube. The liner assembly comprises an inner liner defining a guidewire lumen, and a key attached to a proximal end of the inner liner. The key comprises a guide arm interacting with the guide tube to restrict movement of the liner assembly to non-rotational, translational movement.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Corresponding reference characters indicate corresponding parts throughout the drawings.

DETAILED DESCRIPTION

Figure 1:
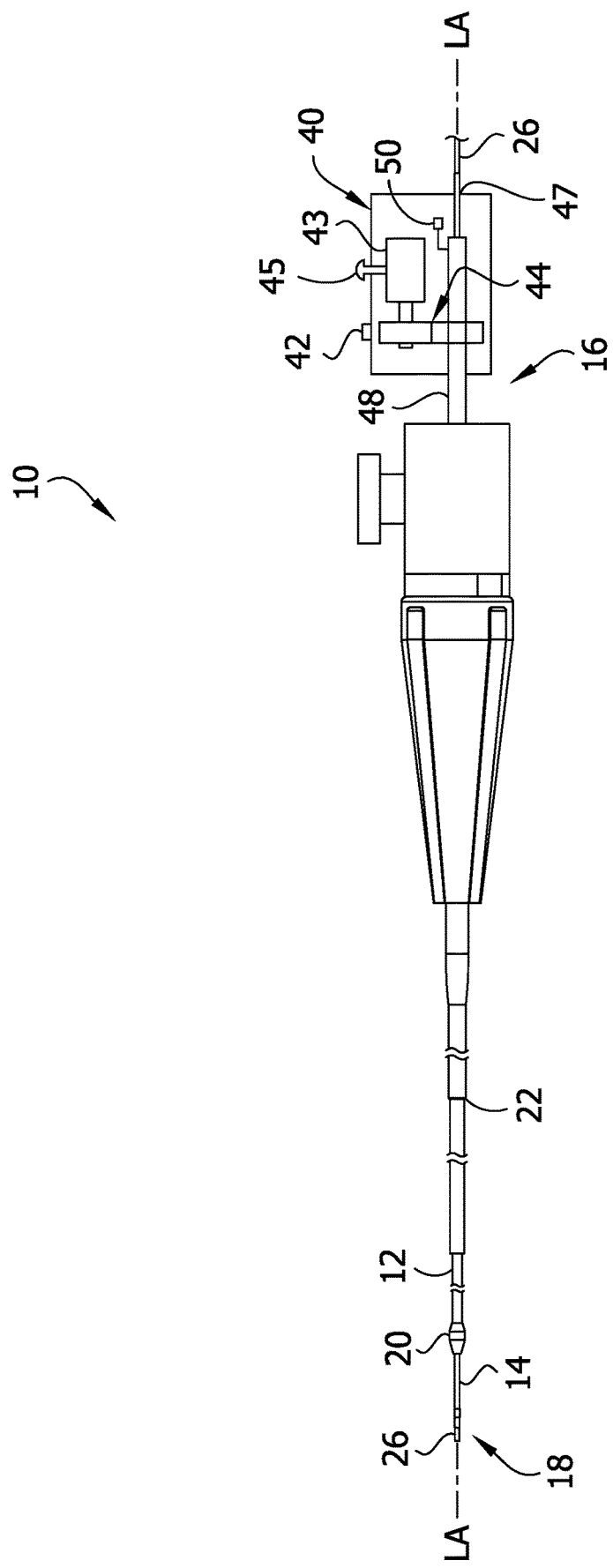
FIG. 1 is a schematic illustration of a catheter of the present disclosure.

Referring to the drawings, and in particular FIG. 1, a rotational tissue-removing catheter for removing tissue in a body lumen is generally indicated at reference number 10. The illustrated catheter 10 is a rotational atherectomy device suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty (PTCA) or the subsequent delivery of a stent. Features of the disclosed embodiments may also be suitable for treating chronic total occlusion (CTO) of blood vessels, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The catheter 10 is sized for being received in a blood vessel of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Figure 2:
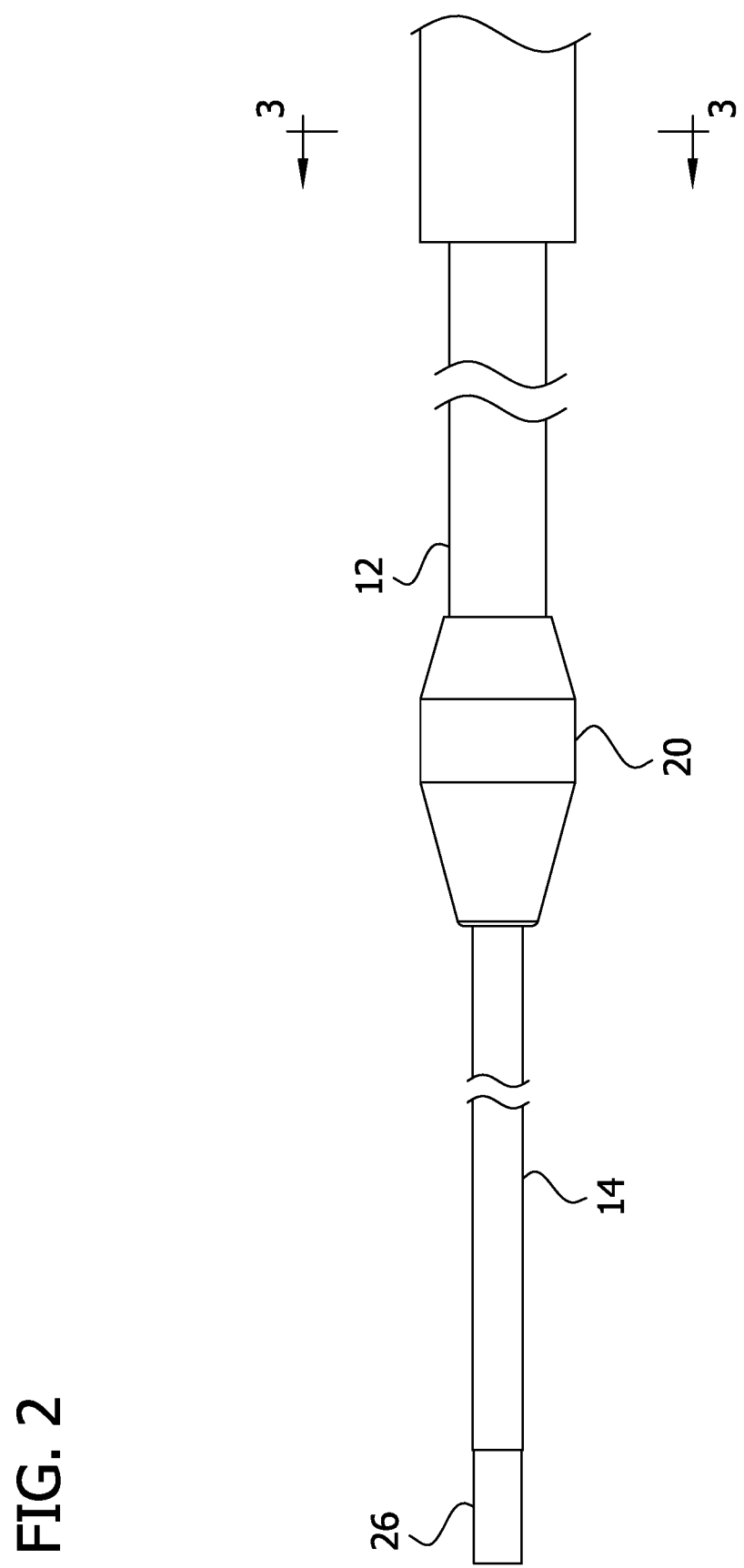
FIG. 2 is an enlarged elevation of a distal end portion of the catheter.
Figure 3:
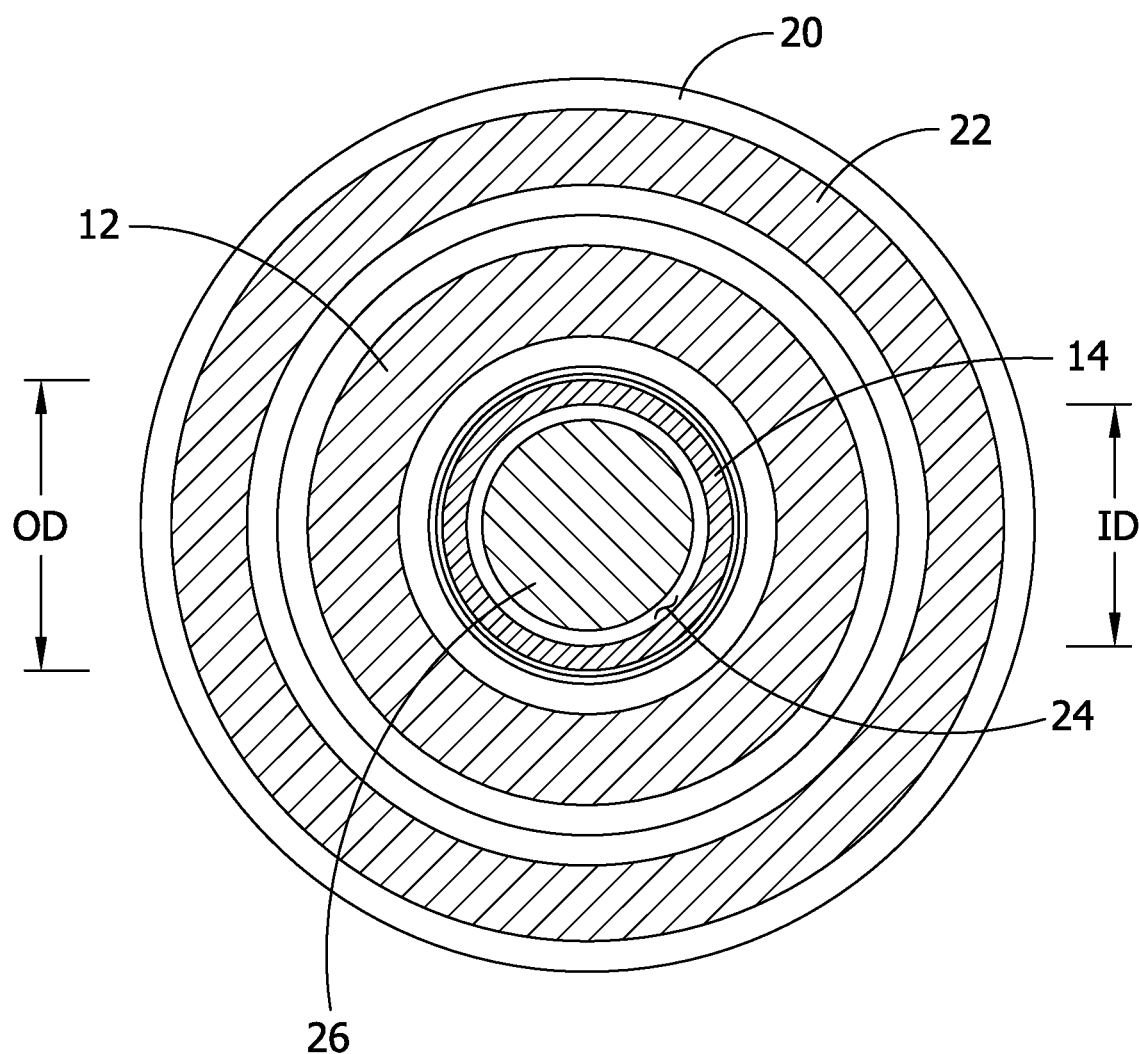
FIG. 3 is a cross section taken through line 3-3 in FIG. 2.

Referring to FIGS. 1-3, the catheter 10 comprises an elongate drive coil 12 (broadly, an elongate body) disposed around an elongate inner liner 14. The drive coil 12 and inner liner 14 extend along a longitudinal axis LA of the catheter from a proximal end portion 16 to a distal end portion 18 of the catheter. A tissue-removing element 20 is disposed on a distal end of the drive coil 12 and is configured for rotation to remove tissue from a body lumen as will be explained in greater detail below. An isolation sheath 22 is disposed around the drive coil 12. The drive coil 12 and the inner liner 14 are both configured to translate relative to the isolation sheath 22. The catheter 10 is sized and shaped for insertion into a body lumen of a subject. The isolation sheath 22 isolates the body lumen from at least a portion of the drive coil 12 and inner liner 14. The inner liner 14 defines a guidewire lumen 24 (FIG. 3) for slidably receiving a guidewire 26 therein so that the catheter 10 can be advanced through the body lumen by traveling along the guidewire. The guidewire can be a standard 0.014-inch outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). In the illustrated embodiment, the guidewire lumen 24 extends along an entire working length of the catheter 10. In one embodiment, the overall working length of the catheter 10 may be between about 135 cm (53 inches) and about 142 cm (56 inches). In use, the guidewire 26 may extend about 40 mm (1.6 inches) past a distal end of the inner liner 14.

Referring to FIGS. 1 and 4-7, the catheter 10 further comprises a handle 40 secured at a proximal end of the isolation sheath 22. The handle 40 comprises a housing 41 that supports the components of the handle. The housing 41 has a generally elongate egg shape and includes a plurality of housing sections secured together to enclose the internal components of the handle 40. In the illustrated embodiment, the housing 41 includes a bottom housing section 41A, a middle housing section 41B secured to the top of the bottom housing section, and a top housing section 41C secured to the top of the middle housing section. In one embodiment, the bottom housing section 41A is removable from the middle housing section 41B to provide access to the components of the handle 40 in the interior of the housing 41 by a user. It will be understood that the housing 41 can have other shapes and configurations without departing from the scope of the disclosure.

The housing 41 supports an actuator 42 (e.g., a lever, a button, a dial, a switch, or other device) configured for selectively actuating a motor 43 disposed in the handle to drive rotation of the drive coil 12, and the tissue-removing element 20 mounted at the distal end of the drive coil. The motor 43 is configured to rotate the drive coil 12 and tissue-removing element 20 at speeds of greater than about 80,000 RPM. The motor 43 is coupled to the drive coil 12 by a gear assembly 44 and drive assembly 48 supported within the housing 41.

The gear assembly 44 comprises a gearbox housing 55 that mounts and at least partially encloses a pair of gears for transferring the rotation of a shaft of the motor 43 to the drive coil 12. A driver gear 81 (FIG. 6) of the gear assembly 44 is attached to the motor shaft (not shown) such that the driver gear rotates with the motor shaft when the motor 43 is activated. A driven gear 83 is in mesh with the driver gear 81 so that rotation of the driver gear causes the driven gear to rotate in the opposite direction. The drive assembly 48 attaches the driven gear 83 to the drive coil 12 so that the rotation of the driven gear causes the drive coil to rotate. The gearbox housing 55 includes a sleeve portion 69 (FIG. 7) on a proximal side of the gearbox housing that receives an end of a guide tube 223. The gearbox housing 55 also attaches to a carriage or advancer frame 73 for moving the motor 43 and gear assembly 44 within the housing 41. Further, attaching the gearbox housing 55 to the advancer frame 73 secures the motor 43 in the advancer frame so that the motor moves along with the advancer frame. A controller 50 may be provided in the handle 40. The controller 50 may be programmed to control operation of the catheter.

It is understood that other suitable actuators, including but not limited to touchscreen actuators, wireless control actuators, automated actuators directed by a controller, etc., may be suitable to selectively actuate the motor in other embodiments. In some embodiments, a power supply may come from a battery (not shown) contained within the handle 40. The battery can provide the current source for the guidewire detection circuit. In other embodiments, the power supply may come from an external source.

Figure 4:
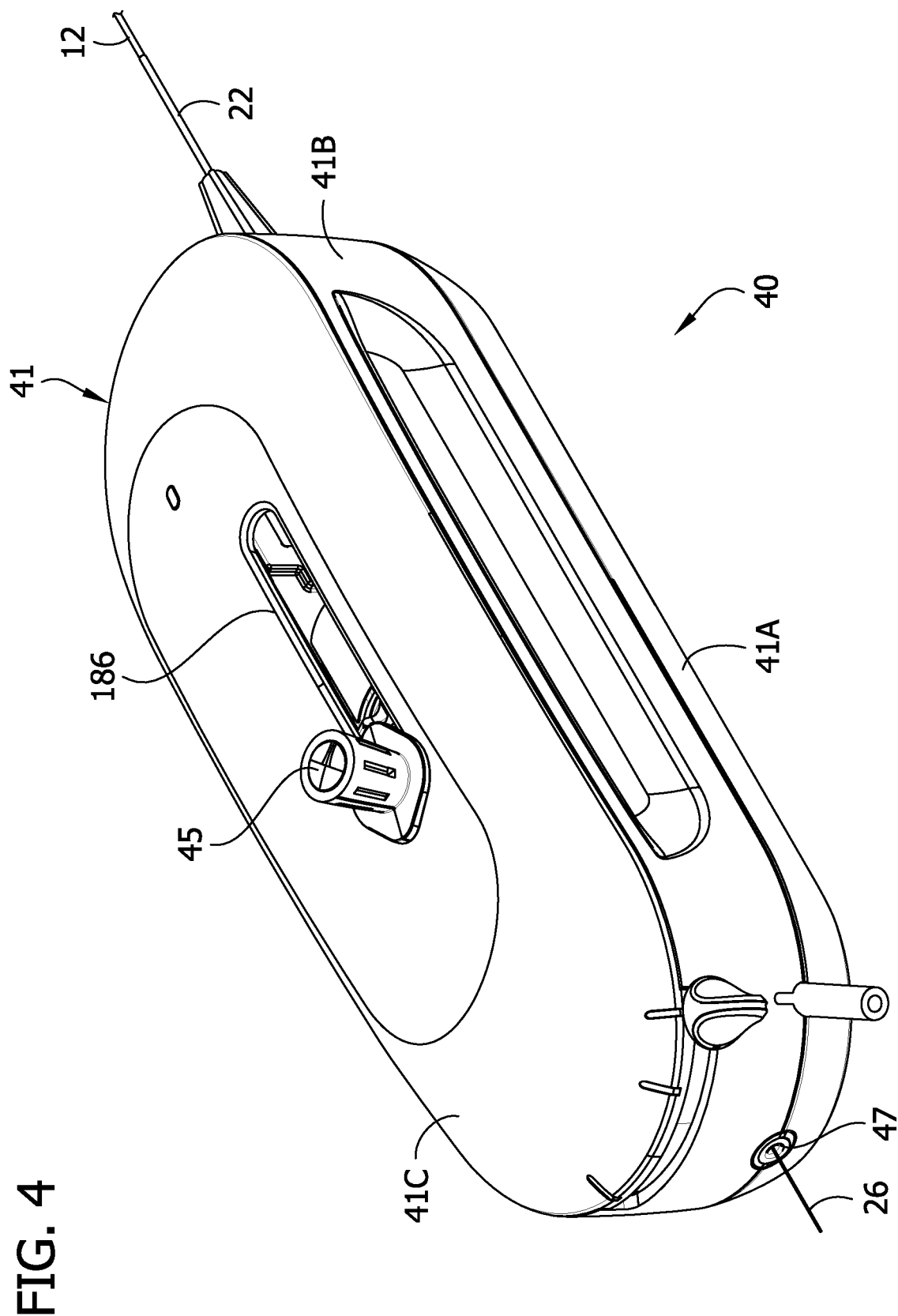
FIG. 4 is a top perspective of a handle of the catheter.
Figure 5:
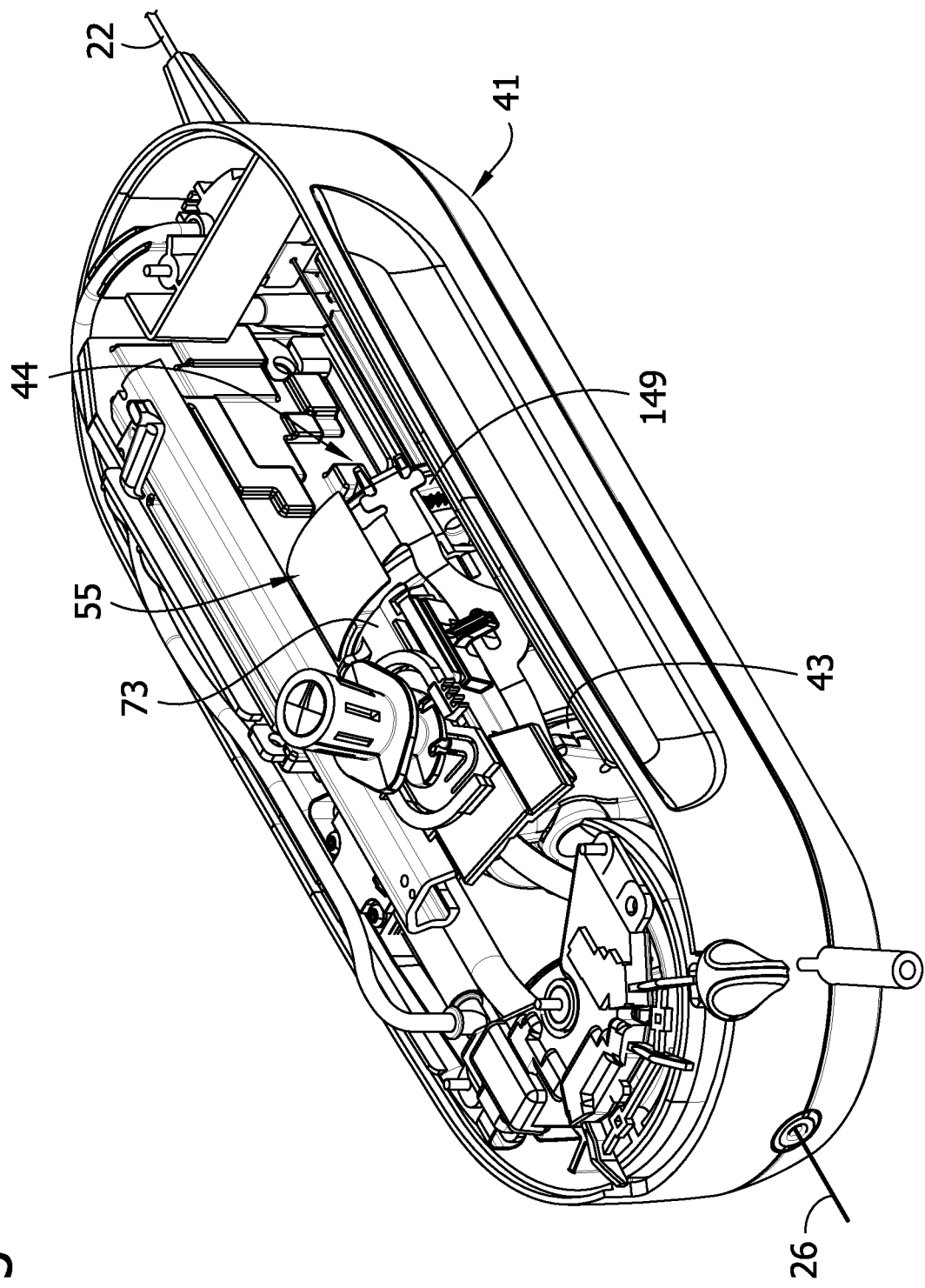
FIG. 5 is a top perspective of the handle with a top housing section removed.
Figure 6:
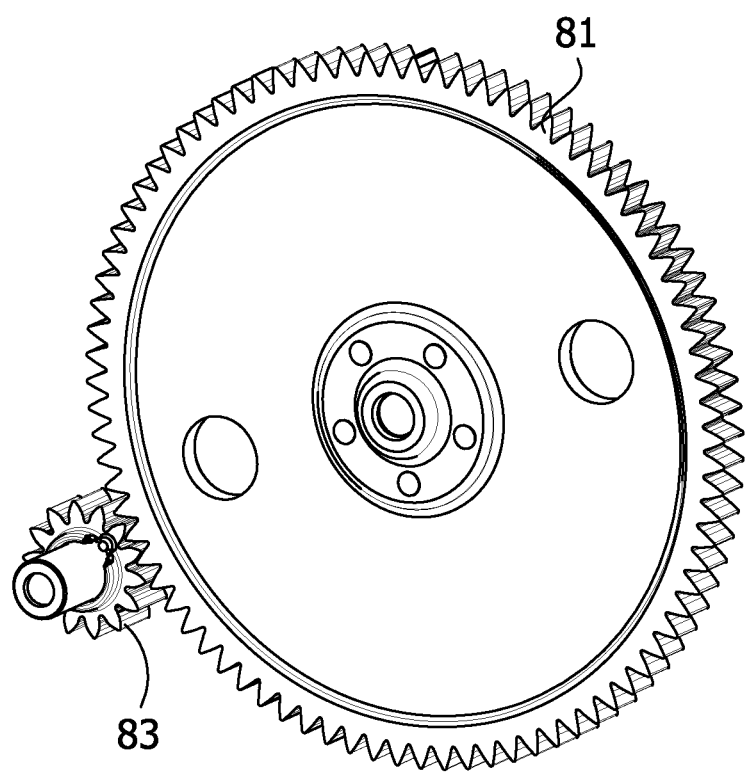
FIG. 6 is a perspective of gears of a gear assembly in the handle.

Referring to FIGS. 1, 4, and 5, an advancer 45 is positioned on the handle 40 and is operatively coupled to the drive coil 12 for movement of the drive coil relative to the handle to advance and retract the drive coil, inner liner 14, and tissue-removing element 20. The housing 41 of the handle 40 may define a slot 186 which limits the movement of the advancer 45 relative to the handle. Thus, the length of the slot 186 determines the amount of relative movement between the inner liner 14 and the handle 40. In one embodiment, the slot has a length of about 70 mm (2.8 inches). The advancer 45 is operatively attached to the advancer frame 73 so that movement of the advancer causes movement of the advancer frame. The advancer frame 73 comprises an arch shaped body configured to slidingly receive the cylindrically shaped motor 43. Bearings 149 (FIG. 5) are mounted on the frame 73. The bearings 149 engage the housing 41 so that the bearings can slide along the housing to facilitate movement of the frame 73 in the housing.

Figure 7:
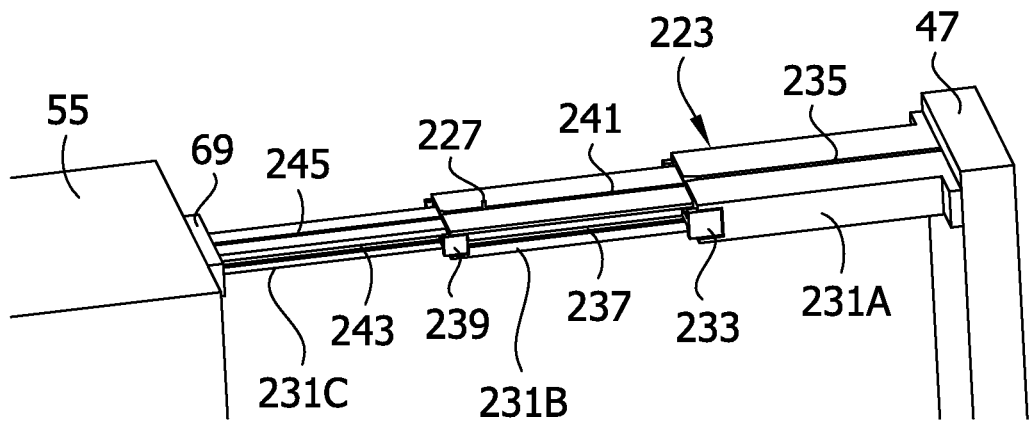
FIG. 7 is an illustration of a guide tube in the handle.
Figure 8:
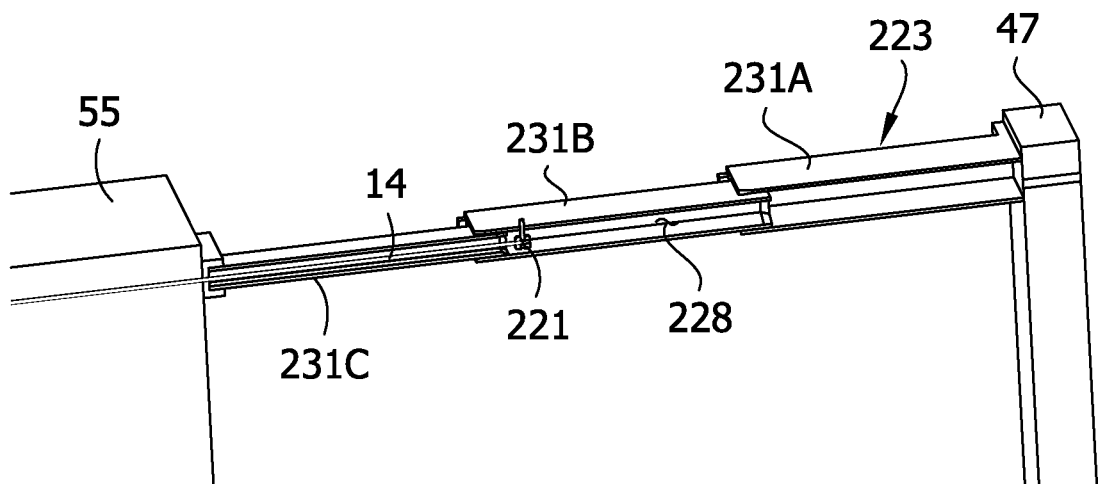
FIG. 8 is an illustration of the guide tube in FIG. 7 with portions of the guide tube removed to show internal detail.
Figure 9:
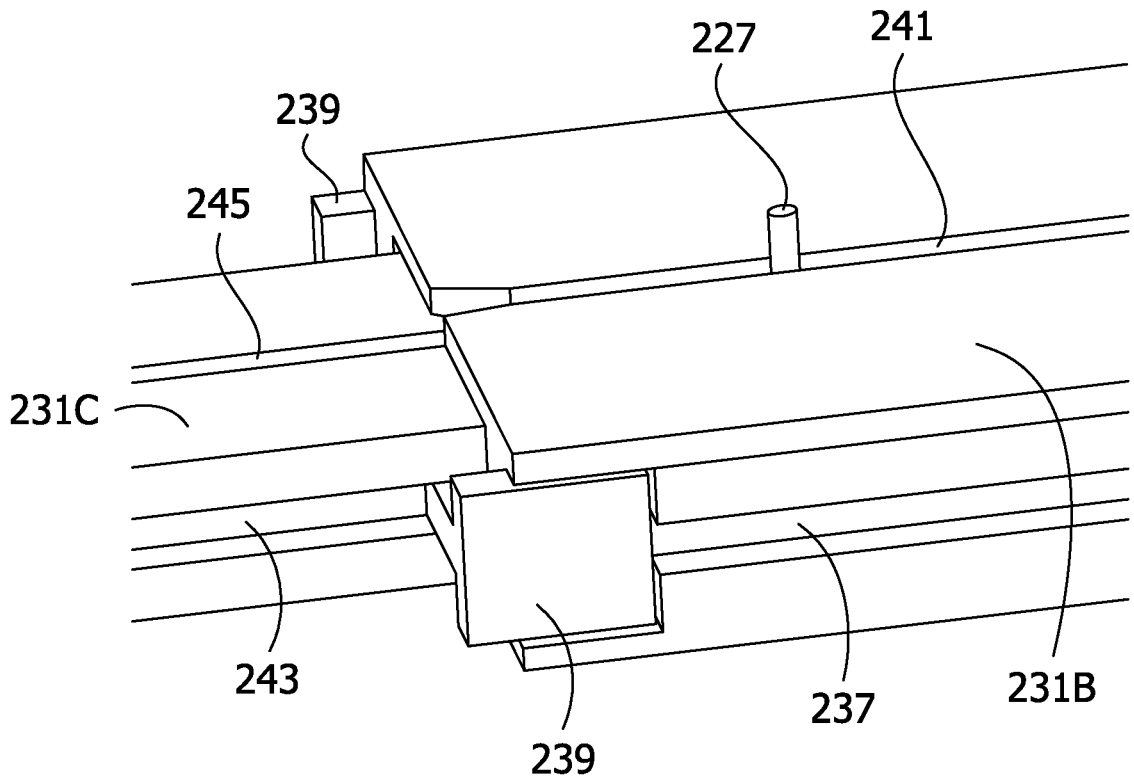
FIG. 9 is an enlarged fragmentary portion of the guide tube in FIG. 7.
Figure 10:
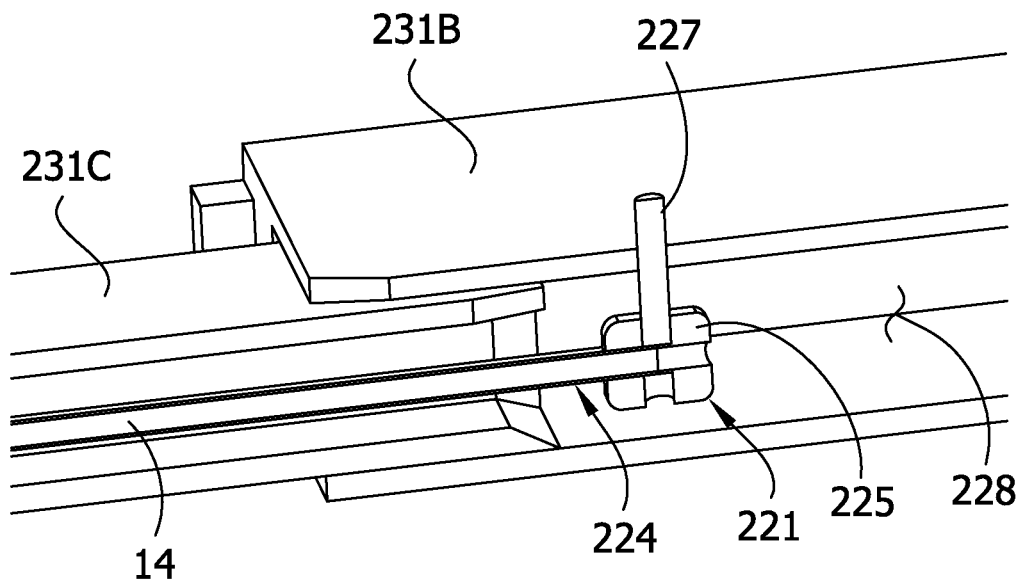
FIG. 10 is the enlarged fragmentary portion of the guide tube in FIG. 9 with portions of the guide tube removed to show internal detail.

Referring to FIGS. 4 and 7, a guidewire port 47 is mounted on a proximal end of the guide tube 223. The guidewire port 47 provides structure in the handle 40 to support the guidewire at the proximal end of the handle. Additionally, a guidewire lock may be provided in the guidewire port 47 to lock the guidewire 26 in place relative to the handle.

Referring to FIGS. 7-10, a liner key 221 is attached to a proximal end of the liner 14 and is received in the guide tube 223 mounted in the handle 40. The engagement between the liner key 221 and the guide tube 223 permits the liner key and liner 14 to translate relative to the guide tube but prevents rotation of the liner key and liner relative to the guide tube. The liner key 221 comprises a semi-cylindrical member 225 (broadly, a base) and an elongate tubular member or mandrel 227 (broadly, a guide arm) extending laterally from the semi-cylindrical member. In the illustrated embodiment, the mandrel 227 extends upward from the semi-cylindrical member 225 generally at a mid-point along a length of the semi-cylindrical member. A passage 229 extends through the liner key 221. A first section of the passage 229 extends vertically through a top and bottom surface of the semi-cylindrical member 225. The mandrel 227 is received in the first section of the passage 229. In particular, the mandrel 227 is received in an opening in the top surface of the semi-cylindrical member 225. A second section of the passage 229 extends longitudinally through the semi-cylindrical member 225. The second section of the passage forms an inner diameter in the semi-cylindrical member 225 of about 0.8 mm. The proximal end of the liner 14 is received and retained in the second section of the passage 229. The liner 14 can be retained in the liner key 221 by any suitable means, including without limitation, glue, thermal bond, and mechanical bond. Thus, the liner key 221 and the liner 14 are configured to co-translate with each other. The mandrel 227 may be similarly secured in the semi-cylindrical member 225. The liner 14 and liner key 221 may be broadly considered a liner assembly 224.

The guide tube 223 extends proximally from the gearbox housing 55 at a distal end of the guide tube to the guidewire port 47 at a proximal end of the guide tube. The guide tube 223 is also attached to the gearbox housing 55 such that movement of the gearbox housing also causes movement of the guide tube. Further, because the gearbox housing 55 is coupled to the advancer 45 via the advancer frame 73, the guide tube 223 is coupled to the advancer 45 through the advancer frame and gearbox housing. Therefore, movement of the advancer 45 causes movement of the guide tube 223 in the handle 40. The gearbox housing 55, and advancer frame 73 may be broadly considered a coupling assembly for coupling the guide tube 223 to the advancer 45.

The guide tube 223 has a passage 228 (FIG. 8) that receives the liner key 221 for non-rotational, translating movement relative to the guide tube. In one embodiment, the guide tube 223 has a non-circular interior passage defined by four planar wall sections. However, the passage 228 could have other interior shapes without departing from the scope of the disclosure. Further, the guide tube 223 comprises a plurality of separate guide sections 231 movably attached to each other such that the guide tube can change its effective length during use of the catheter 10. In the illustrated embodiment, the guide sections 231 are telescopically received within each other to allow the guide tube 223 to extend its length as the gearbox housing 55 is moved distally in the handle 40 and shorten its length as the gearbox housing is moved proximally in the handle. In particular, a first, proximal guide section 231A extends distally from the guidewire port 47 from a proximal end to a distal end. A pair of slides 233 are mounted on the distal end of the proximal guide section 231A. Each slide 233 includes a base and a tab extending inward from the base toward the passage 228. A gap or channel 235 extends longitudinally along a top surface of the proximal guide section 231A. In the illustrated embodiment, the gap 235 extends from the proximal end to the distal end of the proximal guide section 231A. A second, intermediate guide section 231B is telescopically received in the proximal guide section 231A. The intermediate guide section 231B includes a pair of tracks 237 (only one is shown) extending longitudinally along opposite exterior side surfaces of the guide section. In the illustrated embodiment, each track 237 comprises an elongate slot. The tracks 237 are configured to receive tabs of respective slides 233 on the proximal guide section 231A to guide movement of the intermediate guide section 231B relative to the proximal guide section. Similarly, a pair of slides 239 are mounted on the distal end of the intermediate guide section 231B. A gap or channel 241 extends longitudinally along a top surface of the intermediate guide section 231B. In the illustrated embodiment, the gap 241 extends from a proximal end to a distal end of the intermediate guide section 231B. A third, distal guide section 231C is telescopically received in the intermediate guide section 231B. The distal guide section 231C includes a pair of tracks 243 (only one is shown) extending longitudinally along opposite exterior side surfaces of the guide section. The tracks 243 are configured to receive tabs of respective slides 239 on the intermediate guide section 231B to guide movement of the distal guide section 231C relative to the intermediate guide section. A gap or channel 245 extends longitudinally along a top surface of the distal guide section 231C. In the illustrated embodiment, the gap 245 extends from a proximal end to a distal end of the distal guide section 231C. Although there are three disclosed guide sections, it will be understood that more or less guide sections can be used without departing from the scope of the disclosure. Additionally, the guide tube 223 may comprise a single guide section.

The guide tube 223 is configurable such that the intermediate and distal guide sections 231C, 231B can be received in the proximal guide section 231A so that the effective length of the guide tube 223 is the length of the proximal guide section. The effective length of the guide tube 223 can be increased as the distal and intermediate guide section 231C, 231B are pulled out from the proximal guide section 231A. Further, the mandrel 227 of the liner key 221 extends through the gaps 235, 241, 245 in the guide tube 223 to guide movement of the liner assembly 224 in the guide tube. The gaps 235, 241, 245 are sized to allow translational, linear movement of the mandrel 227 along the gaps but prevent lateral (i.e., side-to-side) movement of the mandrel in the gaps. Thus, the liner key 221 and liner 14 are prevented from rotational movement in the guide tube 223. The mechanical connection between the mandrel 227 and the guide tube 223 also absorbs the torsional forces created by the rotating drive coil 12 so that the forces are not transferred to the inner liner 14 and guidewire 26. Accordingly, the rotational forces are not transferred to the tissue-removing element 20 coupled at the distal end of the inner liner 14. This also prevents the guidewire 26 from kinking further reducing the stress on the tissue-removing element 20.

It is envisioned that the liner key 221 and guide tube 223 can have other configurations for permitting relative translation and preventing relative rotation. For instance, in the illustrated embodiment, the liner key 221 includes a single mandrel 227 extending upwards from a top surface of the semi-cylindrical member 225. However, the liner key 221 may include a plurality of mandrels and/or one or more mandrels extending from other locations and in other directions without departing from the scope of the disclosure. Further, any suitable materials may be used for the liner key 221 and guide tube 223. For example, the liner key 221, can be formed from Peek, Polyoxymethylene (POM), or polycarbonate (PC).

Referring to FIGS. 1, and 3, the isolation sheath 22 comprises a tubular sleeve configured to isolate and protect a subject's arterial tissue within a body lumen from the rotating drive coil 12. The isolation sheath 22 is fixed to the handle 40 at a proximal end of the sheath and does not rotate. The isolation sheath 22 provides a partial enclosure for the drive coil 12 and inner liner 14 to move within the sheath. The inner diameter of the isolation sheath 22 is sized to provide clearance for the drive coil 12. The space between the isolation sheath 22 and the drive coil 12 allows for the drive coil to rotate within the sheath and provides an area for saline perfusion between the sheath and drive coil. The outer diameter of the isolation sheath 22 is sized to provide clearance with an inner diameter of a guide catheter (not shown) for delivering the catheter 10 to the desired location in the body lumen. In one embodiment, the isolation sheath 22 has an inner diameter of about 0.050 inches (1.27 mm), an outer diameter of about 0.055 inches (1.4 mm), and a length of about 1500 mm (59 inches). The isolation sheath 22 can have other dimensions without departing from the scope of the disclosure. In one embodiment, the isolation sheath 22 is made from Polytetrafluorethylene (PTFE). Alternatively, the isolation sheath 22 may comprise a multilayer construction. For example, the isolation sheath 22 may comprise an inner layer of perfluoroalkox (PFA), a middle braided wire layer, and an outer layer of Pebax.

Referring to FIGS. 1-3, the drive coil 12 may comprise a tubular stainless steel coil configured to transfer rotation and torque from the motor 43 to the tissue-removing element 20. Configuring the drive coil 12 as a coiled structure allows for the rotation and torque of the drive coil 12 to be applied to the tissue-removing element 20 when the catheter 10 is traversed across a curved path. The coil configuration of the drive coil 12 is also configured to expand its inner diameter when the coil is rotated so that the drive coil remains spaced from the inner liner 14 during operation of the catheter 10. In one embodiment, the drive coil 12 has an inner diameter of about 0.023 inches (0.6 mm) and an outer diameter of about 0.035 inches (0.9 mm). The drive coil 12 may have a single layer construction. For example, the drive coil may comprise a 7 filar (i.e., wire) coil with a lay angle of about 30 degrees. Alternatively, the drive coil 12 could be configured from multiple layers without departing from the scope of the disclosure. For example, the drive coil 12 may comprise a base coil layer and a jacket (e.g., Tecothane™) disposed over the base layer. In one embodiment, the drive coil comprises a 15 filar coil with a lay angle of about 45 degrees. The Tecothane™ jacket may be disposed over the coil. Alternatively, the drive coil 12 may comprise a dual coil layer configuration which also includes an additional jacket layer over the two coil layers. For example, the drive coil may comprise an inner coil layer comprising a 15 filar coil with a lay angle of about 45 degrees, and an outer coil layer comprising a 19 filar coil with a lay angle of about 10 degrees. Drive coils having other configurations are also envisioned.

Referring to FIGS. 1-3 and 11, the inner liner 14 comprises a multiple layer tubular body configured to isolate the guidewire 26 from the drive coil 12 and tissue-removing element 20. The inner liner 14 is extendable through the handle 40 from a position within the handle to a position distal of the handle. In one embodiment, the inner liner 14 is coupled to the components within the handle 40 but is not fixedly attached to the housing 41 to allow translation of the inner liner relative to the housing. The inner liner 14 has an inner diameter that is sized to pass the guidewire 26. The inner liner 14 protects the guidewire from being damaged by the rotation of the drive coil 12 by isolating the guidewire from the rotatable drive coil. The inner liner 14 may also extend past the tissue-removing element 20 to protect the guidewire 26 from the rotating tissue-removing element. Thus, the inner liner 14 is configured to prevent any contact between the guidewire 26 and the rotating components of the catheter 10. Therefore, any metal-to-metal engagement is eliminated by the inner liner 14. This isolation of the drive coil 12 and tissue-removing element 20 from the guidewire 26 also ensures that the rotation of the drive coil and tissue-removing element is not transferred or transmitted to the guidewire. As a result, a standard guidewire 26 can be used with the catheter 10 because the guidewire does not have to be configured to withstand the torsional effects of the rotating components. Additionally, by extending the inner liner 14 through the tissue-removing element 20 and past the distal end of the tissue-removing element, the inner liner stabilizes the tissue-removing element by providing a centering axis for rotation of the tissue-removing element about the inner liner.

Figure 11:
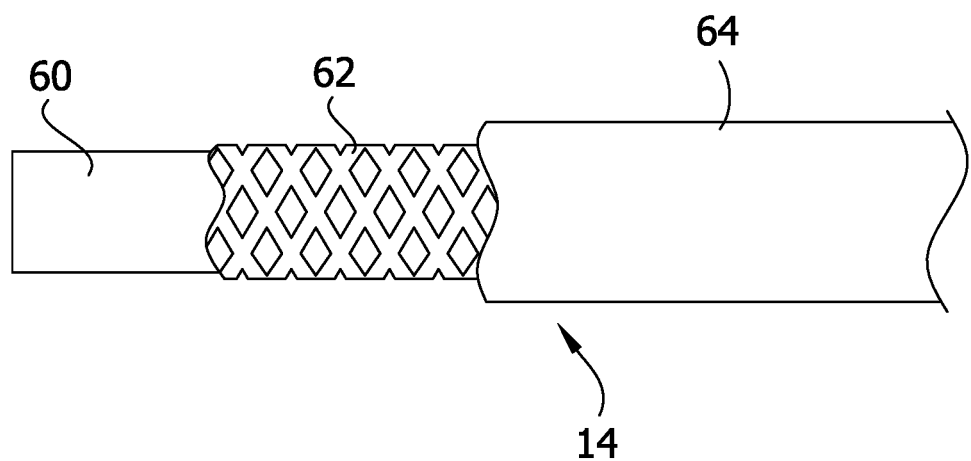
FIG. 11 is a fragmentary elevation of an isolation liner of the catheter with portions broken away to show internal detail.

In the illustrated embodiment, the inner liner 14 comprises an inner PTFE layer 60 an intermediate braided layer 62 comprised of stainless steel, and an outer layer 64 of polyimide (FIG. 11). The PTFE inner layer 60 provides the inner liner 14 with a lubricous interior which aids in the passing of the guidewire 26 though the inner liner. The braided stainless steel intermediate layer 62 provides rigidity and strength to the inner liner 14 so that the liner can withstand the torsional forces exerted on the inner liner by the drive coil 12. In one embodiment, the intermediate layer 62 is formed from 304 stainless steel. The outer polyimide layer 64 provides wear resistance as well as having a lubricous quality which reduces friction between the inner liner 14 and the drive coil 12. Additionally, a lubricious film, such as silicone, can be added to the inner liner 14 to reduce friction between the inner liner and the drive coil 12. In one embodiment, the inner liner 14 has an inner diameter ID of about 0.016 inches (0.4 mm), an outer diameter OD of about 0.019 inches (0.5 mm), and a length of about 59 inches (1500 mm). The inner diameter ID of the inner liner 14 provides clearance for the standard 0.014-inch guidewire 26. The outer diameter OD of the inner liner 14 provides clearance for the drive coil 12 and tissue-removing element 20. Having a space between the inner liner 14 and the drive coil 12 reduces friction between the two components as well as allows for saline perfusion between the components.

Figure 12:
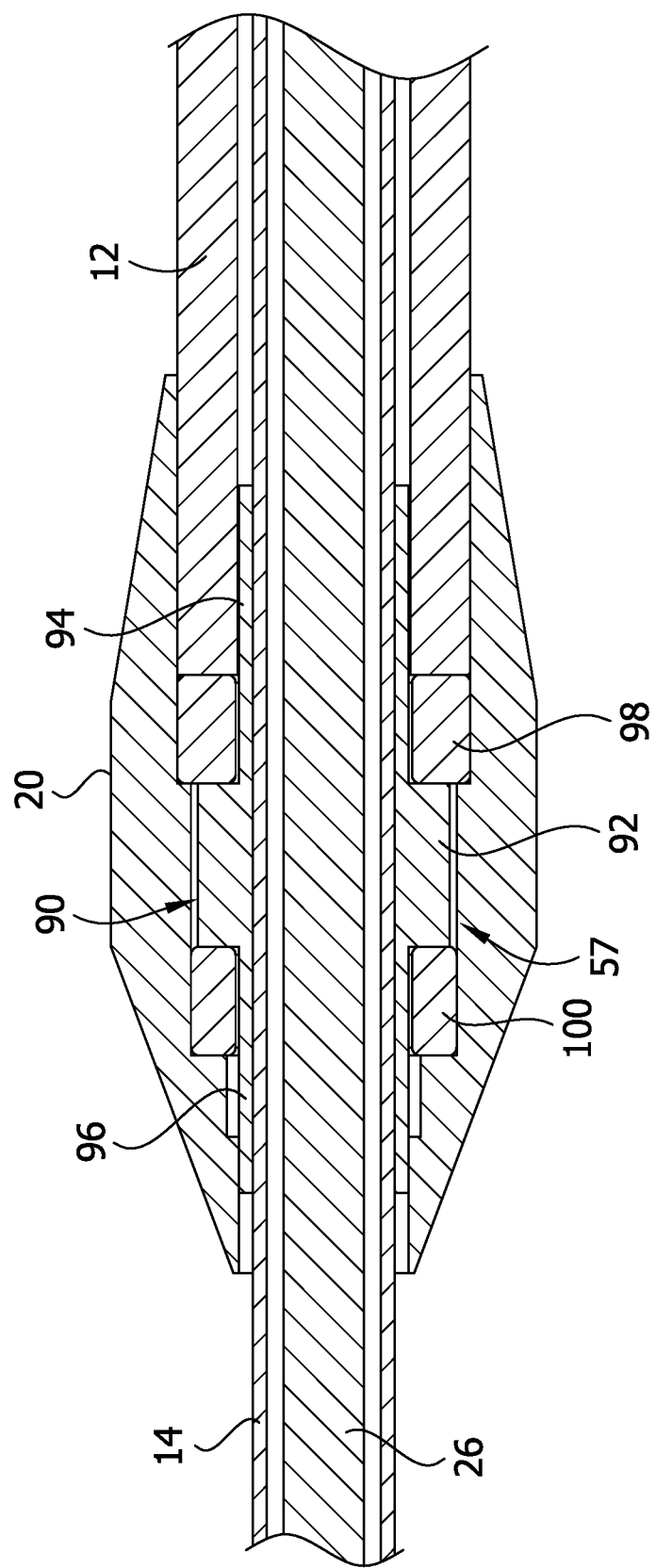
FIG. 12 is an enlarged fragmentary longitudinal cross section of the distal end portion of the catheter in FIG. 2.

Referring to FIGS. 1, 2, and 12, the tissue-removing element 20 extends along the longitudinal axis LA from a proximal end adjacent the distal end portion of the drive coil 12 to an opposite distal end. The tissue-removing element 20 is operatively connected to the motor 43 for being rotated by the motor. When the catheter 10 is inserted into the body lumen and the motor 43 is rotating the tissue-removing element 20, the tissue-removing element is configured to remove occlusive tissue in the body lumen to separate the tissue from the wall of the body lumen. Any suitable tissue-removing element for removing tissue in the body lumen as it is rotated may be used in one or more embodiments. In the illustrated embodiment, the tissue-removing element 20 comprises an abrasive burr configured to abrade tissue in the body lumen when the motor 43 rotates the abrasive burr. The abrasive burr 20 has an abrasive outer surface formed, for example, by a diamond grit coating, surface etching, or the like. In other embodiments, the tissue-removing element can comprise one or more cutting elements having smooth or serrated cutting edges, a macerator, a thrombectomy wire, etc.

Figure 13:
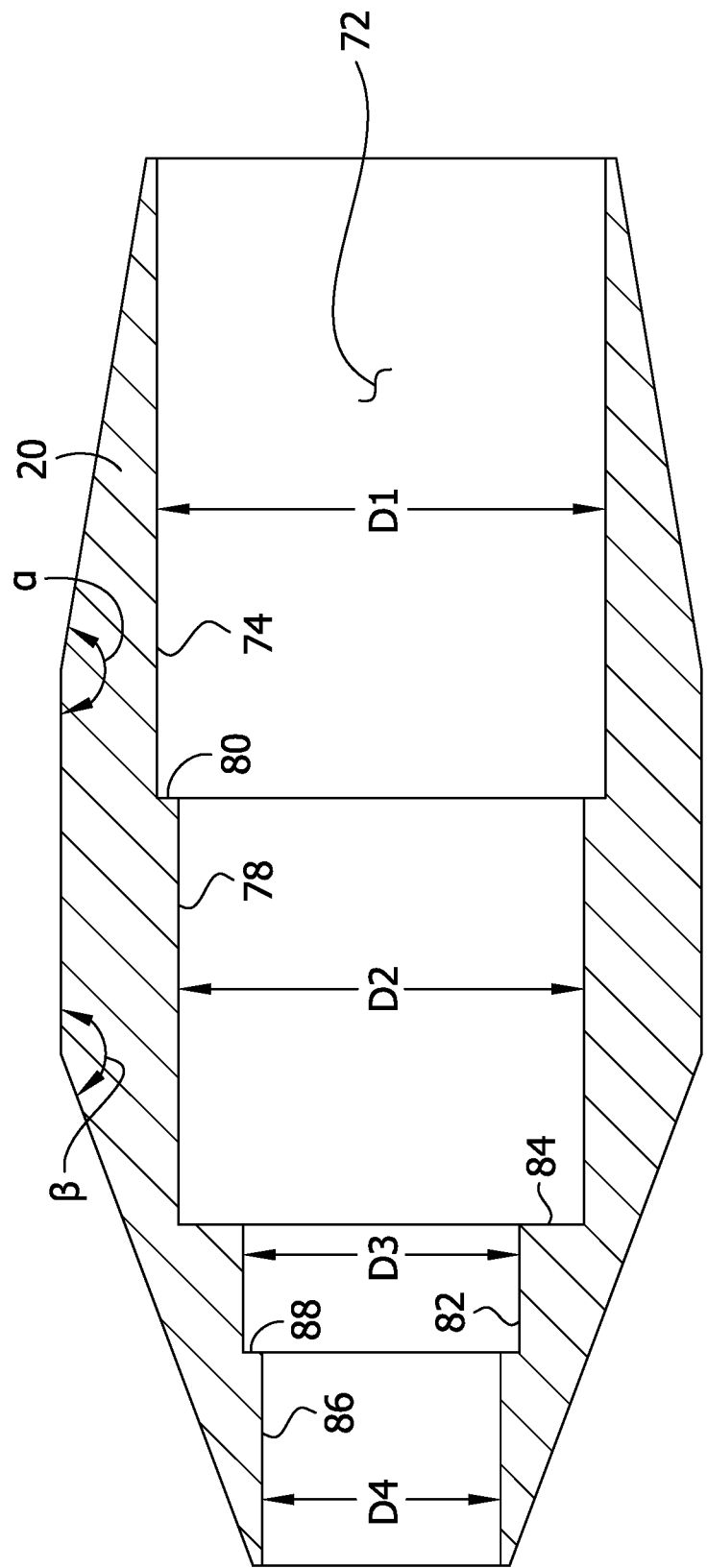
FIG. 13 is an enlarged longitudinal cross section of a tissue-removing element of the catheter.

Referring to FIG. 13, a cavity 72 extends longitudinally through the tissue-removing element 20 such that the tissue-removing element defines openings at its proximal and distal ends. The cavity 72 includes a first diameter portion 74 extending distally from the proximal end of the tissue-removing element 20 and a second diameter portion 78 extending distally from the first diameter portion forming a first shoulder 80 disposed between the first and second diameter portions. A third diameter portion 82 extends distally from the second diameter portion 78 and forms a second shoulder 84 between the second and third diameter portions. A fourth diameter portion 86 extends distally from the third diameter portion to the distal end of the tissue-removing element and forms a third shoulder 88 between the third and fourth diameter portions. The diameters of the first, second, third, and fourth diameter portions 74, 78, 82, 86 are constant along their lengths. In the illustrated embodiment, a diameter D1 of the first diameter portion 74 is larger than a diameter D2 of the second diameter portion 78, the diameter D2 is larger than a diameter D3 of the third diameter portion 82, and the diameter D3 is larger than a diameter D4 of the fourth diameter portion 86. In one embodiment, the diameter D1 of the first diameter portion 74 is about 0.037 inches (0.95 mm), the diameter D2 of the second diameter portion 78 is about 0.035 inches (0.9 mm), the diameter D3 of the third diameter portion 82 is about 0.033 inches (0.85 mm), and the diameter D4 of the fourth diameter portion 86 is about 0.031 inches (0.8 mm). Other cross-sectional dimensions are also envisioned without departing from the scope of the disclosure.

The inner liner 14 extends through the drive coil 12 and past the distal end of the tissue-removing element 20. The fourth diameter portion 86 of the cavity 72 is sized to pass the inner liner 14 with a small clearance. The inner diameter D4 provides clearance between the tissue-removing element 20 and the inner liner 14 to reduce friction between the components. Accordingly, the tissue-removing element 20 is shaped and arranged to extend around at least a portion of the drive coil 12 and inner liner 14 and thus provides a relatively compact assembly for abrading tissue at the distal end portion of the catheter 10.

Figure 14:
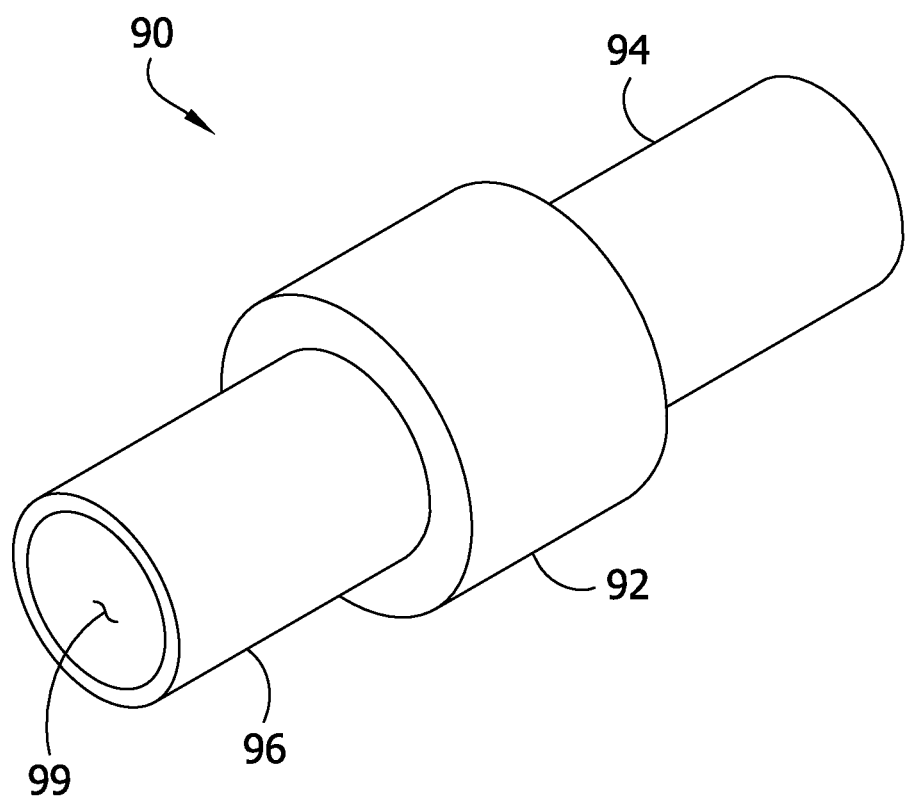
FIG. 14 is a perspective of a bushing of the catheter.

Referring to FIGS. 12-14, a bushing 90 is received in the cavity 72 of the tissue-removing element 20 and around the inner liner 14. The busing 90 comprises a center ring portion 92, a proximal ring portion 94 extending proximally from the center ring portion, and a distal ring portion 96 extending distally from the center ring portion. The ring portions of the bushing 90 define a channel 99 extending through the bushing that receives a portion of the inner liner 14. In the illustrated embodiment, the center ring portion 92 has a larger outer diameter than the proximal and distal ring portions 94, 96. The center ring portion 92 is disposed in the second diameter portion 78 of the cavity 72, the proximal ring portion 94 is disposed in the first diameter portion 74, and the distal ring portion 96 is disposed in the second and third diameter portions 78, 82. In one embodiment, the bushing 90 is made from polyetheretherketone (PEEK) and polytetrafluoroethylene (PTFE). However, the bushing 90 can be formed from other material without departing from the scope of the disclosure.

Figure 15:
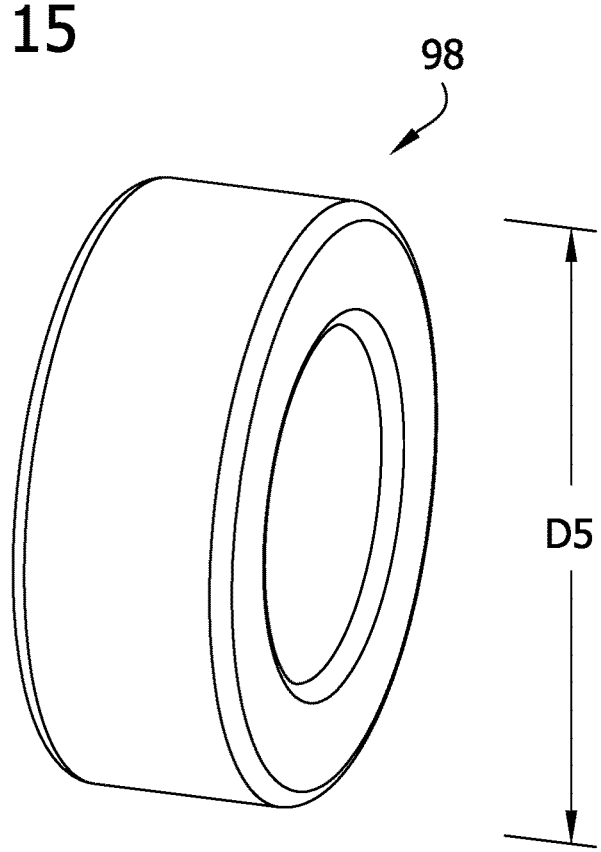
FIG. 15 is a perspective of a first bearing of the catheter.
Figure 16:
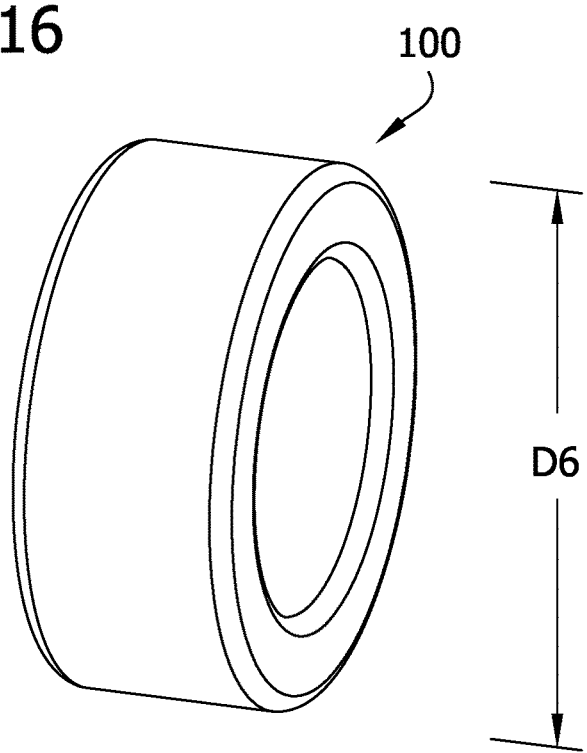
FIG. 16 is a perspective of a second bearing of the catheter.

Referring to FIGS. 12, 15, and 16, a first bearing 98 is disposed around the proximal ring portion 94 of the bearing 90, and a second bearing 100 is disposed around the distal ring portion 96 of the bearing. The first bearing 98 has an outer diameter D5 that is greater than an outer diameter D6 of the second bearing 100. In one embodiment, the bearings 98, 100 are made from Zirconia. The first bearing 98 is disposed in registration with the first diameter portion 74 of the cavity 72 in the tissue-removing element 20 and seats between a distal end of the drive coil 12 at a proximal end of the first bearing, and the center ring portion 92 of the bushing 90 and first shoulder 80 at a distal end of the first bearing. The second bearing 100 is disposed in registration with the second diameter portion 78 of the cavity 72 and is seated between the second shoulder 84 at a distal end of the second bearing, and the center ring portion 92 of the bushing 90 at a proximal end of the second bearing. As such the bushing 90 and bearings 98, 100 are held within the cavity 72 of the tissue-removing element 20. Broadly, the bushing 90 and bearings 98, 100 may be considered a coupling assembly 57 for coupling the inner liner 14 to the tissue-removing element 20.

Referring to FIG. 12, an interior surface of the bushing 90 is fixedly attached to the inner liner 14 such that the inner liner is coupled to the tissue-removing element 20 through the bushing. In one embodiment an adhesive such as an epoxy glue bonds the bushing 90 to the inner liner 14. As such, the bushing 90 does not rotate around the inner liner 14. The drive coil 12 is directly and fixedly attached to the tissue-removing element 20. The tissue-removing element 20 can be fixedly attached to the distal end of the drive coil 12 by any suitable means. In one embodiment, adhesive bonds the drive coil 12 to the tissue-removing element 20. The drive coil 12 is received in the first diameter portion 74 of the cavity 72 and a distal end of the drive coil abuts the first bearing 98. However, the inner liner 14 is not directly attached to the tissue-removing element 20, and the drive coil 12 is not directly attached to the bushing 90, bearings 98, 100, or inner liner. Thus, rotation of the drive coil 12 and tissue-removing element 20 is not transmitted to the inner liner 14 to also rotate the inner liner. Rather the tissue-removing element 20 rotates around the bushing 90 and bearings 98, 100. And because the inner liner is fixedly attached to the bushing 90, which is retained within the cavity 72 of the tissue-removing element 20 by the drive coil 12, the inner liner 14 is coupled to the drive coil and tissue-removing element through the bushing and bearing arrangement.

Referring to FIGS. 1 and 2, to remove tissue in the body lumen of a subject, a practitioner inserts the guidewire 26 into the body lumen of the subject, to a location distal of the tissue that is to be removed. Subsequently, the practitioner inserts the proximal end portion of the guidewire 26 through the guidewire lumen 24 of the inner liner 14 and through the handle 40 so that the guidewire extends through the proximal port 47 in the handle. With the catheter 10 loaded onto the guidewire 26, the practitioner advances the catheter along the guidewire until the tissue-removing element 20 is positioned proximal and adjacent the tissue. When the tissue-removing element 20 is positioned proximal and adjacent the tissue, the practitioner actuates the motor 43 using the actuator 42 to rotate the drive coil 12 and the tissue-removing element mounted on the drive coil. The tissue-removing element 20 abrades (or otherwise removes)

the tissue in the body lumen as it rotates. While the tissue-removing element 20 is rotating, the practitioner may selectively move the drive coil 12 and inner liner 14 distally along the guidewire 26 to abrade the tissue and, for example, increase the size of the passage through the body lumen. The practitioner may also move the drive coil 12 and inner liner 14 proximally along the guidewire 26, and may repetitively move the components in distal and proximal directions to obtain a back-and-forth motion of the tissue-removing element 20 across the tissue by sliding the advancer 45 back and forth within the slot 186 in the handle 40. As the advancer 45 is moved forward, the guide tube 223 may extend in length to provide a sufficient length to guide the movement of the inner liner 14, and key 221 on the inner liner. In particular, the distal movement of the advancer 45 causes the gearbox housing 55 to move distally which pulls on the distal guide section 231C of the telescopic guide tube 223. This may cause the distal guide section 231C and intermediate guide section 231B to move out of the proximal guide section 231A thereby extending the effective length of the guide tube 223 to accommodate the movement of the advancer 45. Conversely, moving the advancer 45 backwards may cause the gearbox housing 55 to push the distal and intermediate guide section 231C, 231B proximally back into proximal guide section 231A thus reducing the effective length of the guide tube 231. Therefore, the guide tube 223 changes its effective length to accommodate the movement of the tissue-removing element 20.

During the abrading process, the bushing 90 and bearings 98, 100 couple the inner liner 14 to the tissue-removing element 20 and allow the drive coil 12 and tissue-removing-element to rotate around the inner liner. The inner liner 14 also isolates the guidewire 26 from the rotating drive coil 12 and tissue-removing element 20 to protect the guidewire from being damaged by the rotating components. As such, the inner liner 14 is configured to withstand the torsional and frictional effects of the rotating drive coil 12 and tissue-removing element 20 without transferring those effects to the guidewire 26. The guided engagement between the guide tube 231 and the liner key 221 also ensures that the torsional forces created by the rotating drive coil 12 are not transferred to the inner liner 14 and guidewire 26. Thus, kinking of the guidewire 26 is prevented. Additionally, this engagement relieves the stress on the bushing 90 and bearings 98, 100 coupling the inner liner 14 to the tissue removing element 20. When the practitioner is finished using the catheter 10, the catheter can be withdrawn from the body lumen and unloaded from the guidewire 26 by sliding the catheter proximally along the guidewire. The guidewire 26 used for the abrading process may remain in the body lumen for use in a subsequent procedure.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:
    an elongate body having an axis, and proximal and distal end portions spaced apart from one another along the axis, wherein the elongate body is sized and shaped to be received in the body lumen;
    a handle mounted to the proximal end portion of the elongate body, the handle comprising a housing enclosing components operable to cause rotation of the elongate body;
    a tissue-removing element mounted on the distal end portion of the elongate body, the tissue-removing element being configured to remove the tissue as the tissue-removing element is rotated by the elongate body within the body lumen;
    an inner liner received within the elongate body and defining a guidewire lumen;
    an advancer mounted on the handle and movable relative to the housing;
    a guide tube mounted in the handle and coupled to the advancer such that distal movement of the advancer relative to the handle causes distal movement of the guide tube, the elongate body, the tissue-removing element, and the inner liner,
    wherein a proximal end of the inner liner is received in the guide tube within the handle and is movable distally relative to the guide tube and the handle, as the advancer is moved distally relative to the handle; and a motor in the handle and operatively engaging the elongate body for driving rotation of the elongate body and tissue-removing element mounted on the elongate body, and a gear assembly operatively connected to the motor, the gear assembly including a gearbox housing, wherein a distal end of the guide tube is attached to the gearbox housing.

2. The tissue-removing catheter as set forth in claim 1, further comprising a coupling assembly coupling the guide tube to the advancer.

3. The tissue-removing catheter as set forth in claim 1, further comprising a carriage mounting the motor in the handle and connecting the advancer to the gearbox housing.

4. The tissue-removing catheter as set forth in claim 1, wherein the guide tube comprising a plurality of separate guide tube sections.

5. The tissue-removing catheter as set forth in claim 1, wherein the inner liner is coupled to the tissue-removing element at a distal end portion of the inner liner.

6. The tissue-removing catheter as set forth in claim 1, wherein the proximal end of the inner liner is movable distally away from a proximal end of the handle as the advancer is moved distally relative to the handle.

7. A tissue-removing catheter for removing tissue in a body lumen, the tissue-removing catheter comprising:
    an elongate body having an axis, and proximal and distal end portions spaced apart from one another along the axis, wherein the elongate body is sized and shaped to be received in the body lumen;
    a handle mounted to the proximal end portion of the elongate body, the handle comprising a housing enclosing components operable to cause rotation of the elongate body;
    a tissue-removing element mounted on the distal end portion of the elongate body, the tissue-removing element being configured to remove the tissue as the tissue-removing element is rotated by the elongate body within the body lumen;

a guide tube mounted in the handle, wherein the guide tube comprising a plurality of separate guide tube sections, wherein each guide tube section defines a longitudinal channel extending from a proximal end of the guide tube section to a distal end of the guide tube section;

an inner liner received within the guide tube and movable relative to the guide tube, the guide tube being configured to extend an effective length of the guide tube to accommodate movement of the inner liner in the guide tube; and a key attached to a proximal end of the inner liner, the key and inner liner being movable in the guide tube, and the key comprising a guide arm configured to extend through the channels in the guide tube sections to restrict movement of the inner liner and key to non-rotational, translational movement.

8. The tissue-removing catheter as set forth in claim 7, wherein at least one of the guide tube sections is telescopically received in another of the guide tube sections such that said at least one of the guide tube sections can move relative to said another of the guide tube sections to extend the effective length of the guide tube.

9. The tissue-removing catheter as set forth in claim 8, wherein said at least one of the guide tube sections includes a track, and said another guide tube section includes a slide movable along the track to guide movement of said at least one of the guide tube sections relative to said another guide tube section.

10. The tissue-removing catheter as set forth in claim 9, wherein the slide comprises a tab received in the track to slide along the track to guide movement of said at least one of the guide tube sections relative to said another guide tube section.

11. A tissue-removing catheter for removing tissue in a body lumen, the tissue-removing catheter comprising:

an elongate body having an axis, and proximal and distal end portions spaced apart from one another along the axis, wherein the elongate body is sized and shaped to be received in the body lumen;

a handle mounted to the proximal end portion of the elongate body, the handle comprising a housing enclosing components operable to cause rotation of the elongate body;

a tissue-removing element mounted on the distal end portion of the elongate body, the tissue-removing element being configured to remove the tissue as the tissue-removing element is rotated by the elongate body within the body lumen;

a guide tube mounted in the handle; and a liner assembly coupled to the guide tube and movable relative to the guide tube, the liner assembly comprising an inner liner defining a guidewire lumen, and a key attached to a proximal end of the inner liner, the key comprising a guide arm interacting with the guide tube to restrict movement of the liner assembly to non-rotational, translational movement.

12. The tissue-removing catheter as set forth in claim 11, wherein the guide tube defines a channel extending longitudinally along a length of the guide tube, the guide arm being received in the channel.

13. The tissue-removing catheter as set forth in claim 12, wherein the guide tube comprising a plurality of separate guide tube sections, each guide tube section defining a portion of the channel.

14. The tissue-removing catheter as set forth in claim 13, where the channel defined by each guide tube section extends from a proximal end of the guide tube section to a distal end of the guide tube section.

15. The tissue-removing catheter as set forth in claim 11, wherein the key comprises a base having a longitudinal axis, the guide arm extending laterally from the base.

* * * * *